United States Patent
Nock

(10) Patent No.: US 11,553,903 B2
(45) Date of Patent: Jan. 17, 2023

(54) CORE NEEDLE BIOPSY DEVICE FOR COLLECTING MULTIPLE SAMPLES IN A SINGLE INSERTION

(71) Applicant: Devicor Medical Products, Inc., Cincinnati, OH (US)

(72) Inventor: Andrew P. Nock, Dayton, OH (US)

(73) Assignee: Devicor Medical Products, Inc., Cincinnati, OH (US)

(*) Notice: Subject to any disclaimer, the term of this patent is extended or adjusted under 35 U.S.C. 154(b) by 614 days.

(21) Appl. No.: 16/525,812

(22) Filed: Jul. 30, 2019

(65) Prior Publication Data

US 2020/0038002 A1 Feb. 6, 2020

Related U.S. Application Data

(60) Provisional application No. 62/712,470, filed on Jul. 31, 2018.

(51) Int. Cl.
*A61B 10/02* (2006.01)

(52) U.S. Cl.
CPC .. *A61B 10/0275* (2013.01); *A61B 2010/0208* (2013.01); *A61B 2010/0225* (2013.01)

(58) Field of Classification Search
CPC ........ A61B 10/0275; A61B 2010/0208; A61B 2010/0225; A61B 10/0283
See application file for complete search history.

(56) References Cited

U.S. PATENT DOCUMENTS

| | | | |
|---|---|---|---|
| 5,394,887 A * | 3/1995 | Haaga | A61B 10/0275 606/167 |
| 5,511,556 A | 4/1996 | De Santis | |
| 5,526,822 A | 6/1996 | Burbank et al. | |
| 5,560,373 A | 10/1996 | De Santis | |
| 5,649,547 A * | 7/1997 | Ritchart | A61B 10/0266 600/566 |
| 5,817,033 A | 10/1998 | De Santis et al. | |
| 6,086,544 A | 7/2000 | Hibner et al. | |
| 6,162,187 A | 12/2000 | Buzzard et al. | |
| 6,432,065 B1 | 8/2002 | Burdorff et al. | |
| 6,514,215 B1 * | 2/2003 | Ouchi | A61B 10/04 600/564 |
| 6,890,308 B2 | 5/2005 | Islam | |
| 7,442,171 B2 | 10/2008 | Stephens et al. | |

(Continued)

FOREIGN PATENT DOCUMENTS

EP 0966920 12/1999

OTHER PUBLICATIONS

Hahn, Markus et al., "Vacuum Assisted Breast Biopsy with Manunotome®," available Nov. 11, 2012, copyright 2013 by Devicor Medical Germany GmbH, published in Germany by Springer Medizin Verlag. 128 pages.

(Continued)

*Primary Examiner* — Sean P Dougherty
(74) *Attorney, Agent, or Firm* — Frost Brown Todd LLP

(57) ABSTRACT

A core needle biopsy device includes a body, a needle assembly and a drive assembly. The needle assembly extends distally from the body and includes a hollow piercer and a hollow cutter. The piercer is disposed within the cutter. The cutter includes a distal tip and a swaged portion proximate the distal tip. The drive assembly is configured to selectively cock and fire the piercer and the cutter.

20 Claims, 17 Drawing Sheets

(56) References Cited

U.S. PATENT DOCUMENTS

| | | |
|---|---|---|
| 7,854,706 B2 | 12/2010 | Hibner |
| 7,938,786 B2 | 5/2011 | Ritchie et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,702,623 B2 | 4/2014 | Parihar et al. |
| 8,858,465 B2 | 10/2014 | Fiebig |
| 9,326,755 B2 | 5/2016 | Fiebig et al. |
| 9,332,970 B2 | 5/2016 | Beck et al. |
| 9,414,816 B2 * | 8/2016 | Rhad ................ A61B 10/0275 |
| 9,700,287 B2 | 7/2017 | McGhie et al. |
| 10,058,309 B2 | 8/2018 | Hatta et al. |
| 2003/0229293 A1 * | 12/2003 | Hibner ............... A61B 10/0283 600/567 |
| 2004/0068231 A1 * | 4/2004 | Blondeau .......... A61B 10/0275 604/157 |
| 2006/0074342 A1 * | 4/2006 | Hibner ............... A61B 10/0275 600/568 |
| 2006/0074343 A1 * | 4/2006 | Hibner ............... A61B 10/0266 600/568 |
| 2006/0074345 A1 | 4/2006 | Hibner |
| 2007/0010843 A1 | 1/2007 | Green |
| 2007/0055173 A1 * | 3/2007 | DeLonzor .......... A61B 10/0266 600/568 |
| 2009/0131821 A1 | 5/2009 | Speeg et al. |
| 2009/0227893 A1 * | 9/2009 | Coonahan .......... A61B 10/0283 600/566 |
| 2010/0152610 A1 | 6/2010 | Parihar et al. |
| 2010/0160819 A1 | 6/2010 | Parihar et al. |
| 2010/0317995 A1 * | 12/2010 | Hibner ............... A61B 10/0275 600/564 |
| 2011/0152715 A1 * | 6/2011 | Delap ................ A61B 10/0275 600/566 |
| 2012/0022397 A1 * | 1/2012 | Jarial ................ A61B 10/0275 600/567 |
| 2012/0302914 A1 * | 11/2012 | Hibner ............... A61B 10/0241 600/567 |
| 2013/0324882 A1 | 12/2013 | Mescher |
| 2017/0035398 A1 * | 2/2017 | Park .................. A61B 10/0283 |
| 2019/0029758 A1 * | 1/2019 | Householder ...... A61B 17/3403 |
| 2019/0231325 A1 * | 8/2019 | Nock ................ A61B 10/0275 |
| 2019/0388073 A1 * | 12/2019 | Larson ............... A61B 10/0266 |
| 2022/0079568 A1 * | 3/2022 | Van Liere .......... A61B 10/0275 |

OTHER PUBLICATIONS

Partial International Search Report and Written Opinion dated Oct. 22, 2019 for Application No. PCT/US2019/044043, 12 pages.

\* cited by examiner

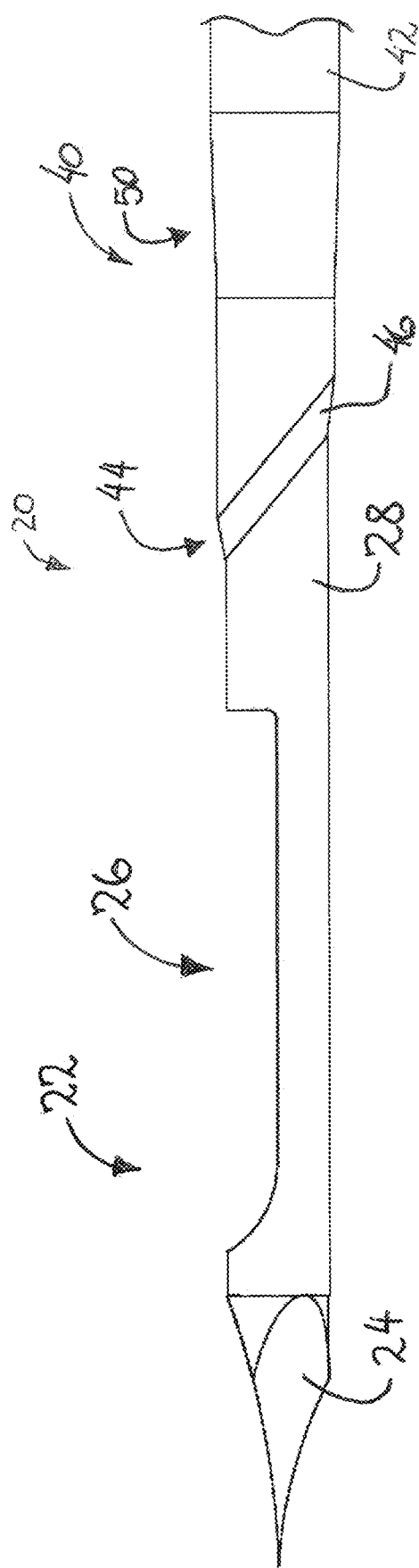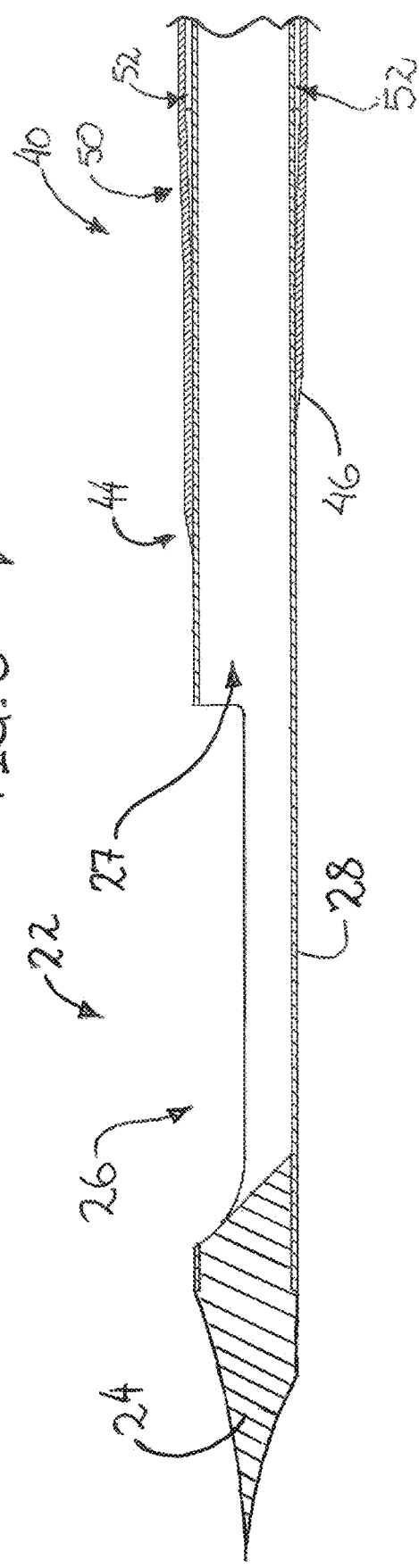
FIG. 3
FIG. 4

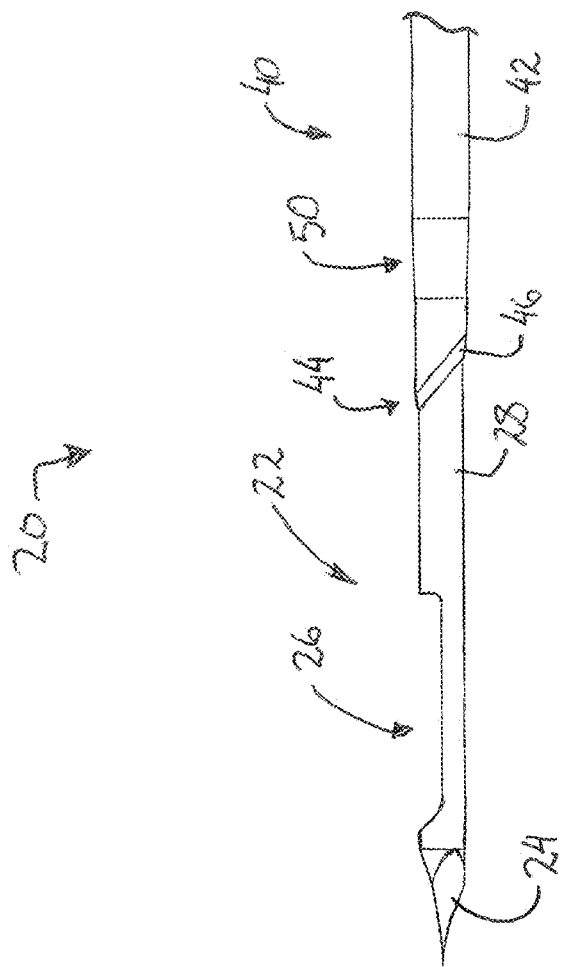
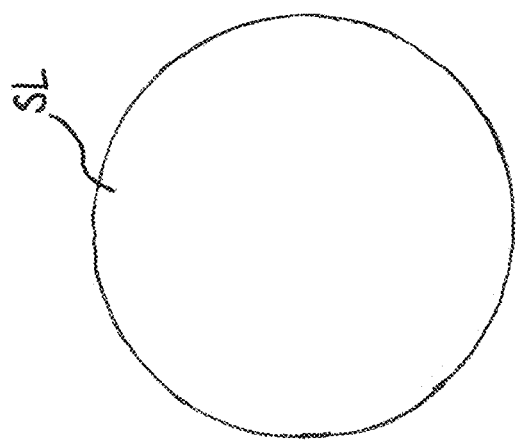
Fig. 12A

CORE NEEDLE BIOPSY DEVICE FOR COLLECTING MULTIPLE SAMPLES IN A SINGLE INSERTION

PRIORITY

This application claims priority to U.S. Provisional Patent App. No. 62/712,470 entitled "Core Needle Biopsy Device for Collecting Multiple Samples in a Single Insertion," filed on Jul. 31, 2018, the disclosure of which is incorporated by reference herein.

BACKGROUND

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

One technique for collecting a breast biopsy is to use a core needle biopsy device. Core needle biopsy devices frequently use a sharp, solid piercer equipped with a lateral tissue receiving notch positioned adjacent to the distal end of the piercer. When tissue is received within the notch, an elongate hollow cutting sheath is translated over the notch to sever a tissue sample. The severed tissue sample is then stored within the notch until both the piercer and the cutting sheath are removed from the patient. Thus, in core-needle biopsy devices, only one tissue sample can be collected per insertion of the piercer and cutting sheath.

Another technique for conducting a breast biopsy is to conduct a breast biopsy using a vacuum-assisted breast biopsy device. In contrast to core needle breast biopsy procedures, vacuum-assisted breast biopsy devices permit the probe to remove multiple samples without requiring the probe be removed from the breast after every sample is collected. For instance, in a vacuum assisted breast biopsy device, a hollow needle is used to penetrate tissue. The hollow needle includes a lateral aperture adjacent to a sharp distal tip. A hollow cutter is disposed within the hollow needle and is moved axially relative to the lateral aperture of the needle to sever tissue samples. Once a tissue sample is severed by the hollow cutter, the tissue sample is transported axially though the cutter and collected in a tissue collection feature.

Examples of vacuum assisted biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 1, 2012; and U.S. Pat. No. 8,206,316, entitled "Tetherless Biopsy Device with Reusable Portion," issued on Jun. 26, 2012. The disclosure of each of the above-cited U.S. Patents is incorporated by reference herein.

Exemplary core needle biopsy devices are disclosed in U.S. Pat. No. 5,560,373, entitled "Needle Core Biopsy Instrument with Durable or Disposable Cannula Assembly," issued on Oct. 1, 1996; U.S. Pat. No. 5,817,033, entitled "Needle Core Biopsy Device," issued on Oct. 6, 1998; and U.S. Pat. No. 5,511,556, entitled "Needle Core Biopsy Instrument," issued on Apr. 30, 1996. The disclosure of each of the above-cited U.S. Patents is incorporated by reference herein.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 3 depicts a side elevational view of the needle assembly of FIG. 2;

FIG. 4 depicts a side cross-section view of the needle assembly of FIG. 2, the cross-section taken along line 4-4 of FIG. 2;

FIG. 12A depicts a side elevational view of the needle assembly of FIG. 2, with the needle assembly positioned proximate to a suspicious lesion;

Figure 1:
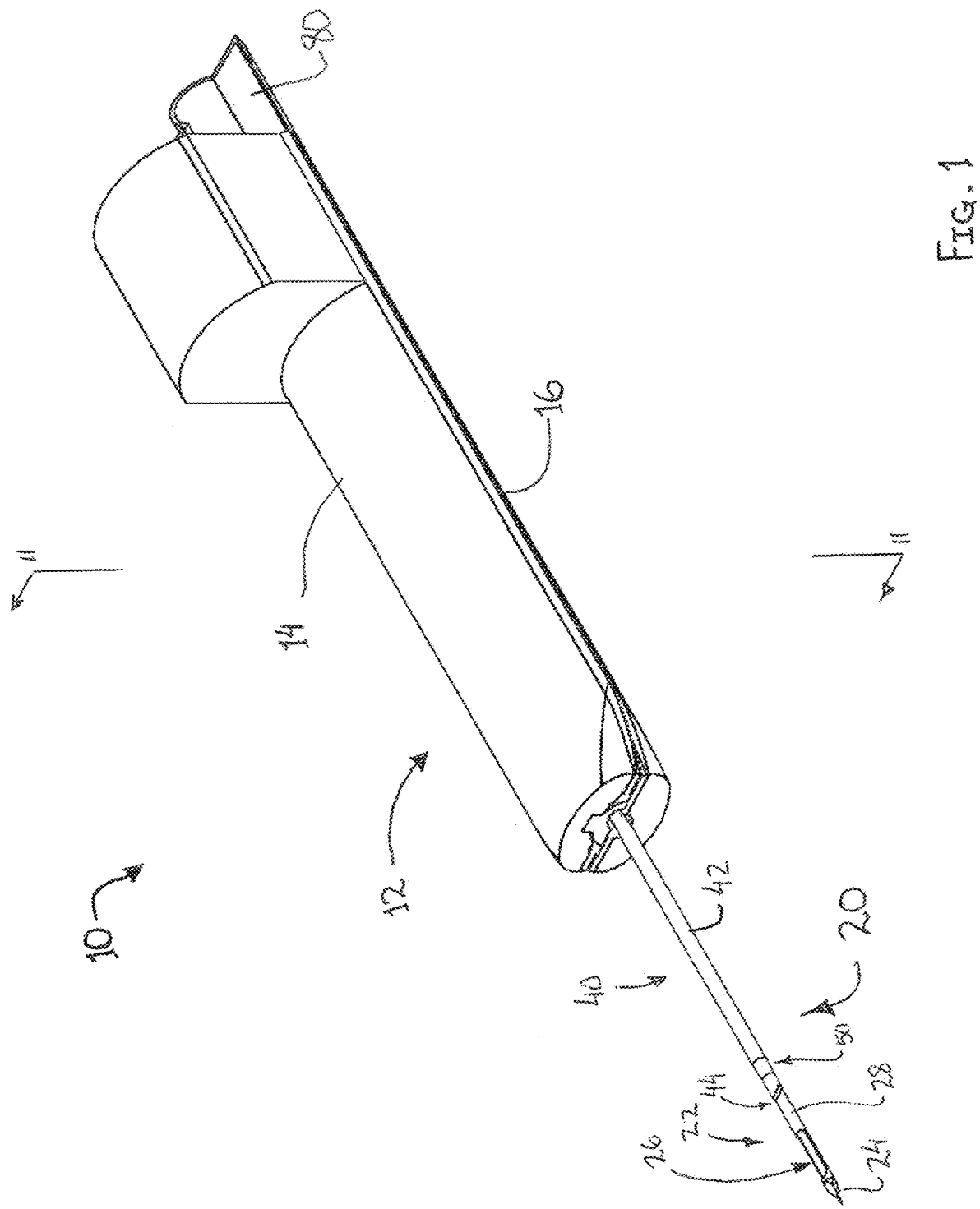
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into the single tissue sample basket. In some other instances, tissue samples are collected into a tissue sample holder having separate compartments for each collected tissue sample. Such a multi-compartment tissue sample holder may additionally include trays or strips that individually hold each tissue sample separately from the other tissue samples. Such trays or strips may be removable or otherwise separable from the tissue sample holder at the conclusion of a biopsy procedure.

Regardless of the structure in which the tissue samples are stored, tissue samples may be collected using biopsy devices under the guidance of various imaging modalities such as ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following text briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an Mill image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Vacuum assisted biopsy devices and core needle biopsy devices both may have various advantages over the other, depending on context. For instance, one advantage of vacuum assisted biopsy devices is that vacuum assistance permits removal of multiple tissue samples using a single insertion. However, while core needle biopsy devices lack this feature, use of core needle biopsy devices may still be desirable. For instance, core needle biopsy devices are generally capable of having smaller needles relative to core needle biopsy devices, thereby reducing patient anxiety and increasing the capacity of the needle to penetrate a lesion. Therefore, in some instances it may be desirable to incorporate the feature of multiple sample removal of a vacuum assisted biopsy device into a core needle biopsy device to achieve the benefits present in both styles of biopsy device.

A desirable feature of the device described herein, which is a core needle biopsy device is that the device allows for single insertion with multiple samples being obtained whilst using a core needle type device. Currently, it is believed that only vacuum assisted biopsy devices have this ability.

FIG. 1 shows an exemplary core needle biopsy device (10) for use in a breast biopsy procedure. Core needle biopsy device (10) of the present example comprises a body (12) and a needle assembly (20) extending distally from body (12). Body (12) includes a holster housing (14) and a probe housing (16). As will be describe in greater detail below, holster housing (14) and probe housing (16) enclose various components of biopsy device (10), which are used to drive needle assembly (20) through a cutting cycle and a tissue acquisition cycle. For instance, in some examples holster housing (14) can enclose more expensive or durable parts such that holster housing (14) can be reused. Similarly, probe housing (16) can enclose less expensive or less durable parts such that probe housing (16) (along with needle assembly (20) can be disposable. When coupled together, holster housing (14) and probe housing (16) of the present example are configured to couple together such that body (12) is sized and shaped for grasping by an operator using a single hand. Although the terms "holster" and "probe" used herein may imply that one part receives another part, it should be understood that no such limitation is intended. For instance, in some examples certain components of holster housing (14) can be received within probe housing (16).

Biopsy device (10) further includes a tissue sample holder (80) disposed at the distal end of body (12). Tissue sample holder (80) of the present example is generally configured as a hollow compartment that can receive tissue samples severed by needle assembly (20). Although not shown, it should be understood that in some examples tissue sample holder (80) can include a basket to hold the collected tissue samples and/or strain fluids from the severed tissue samples. In still other examples, such a basket can be segregated into different compartments to store tissue samples in an organized configuration. In such examples, the basket can be movable to aid in depositing severed tissue samples into a particular compartment. Additionally, it should be understood that in some examples tissue sample holder (80) is in communication with a vacuum source to aid in transporting tissue samples to tissue sample holder (80). Of course, various other alternative configurations of tissue sample holder (80) will be apparent to those of ordinary skill in the art in view of the teachings herein.

Figure 2:
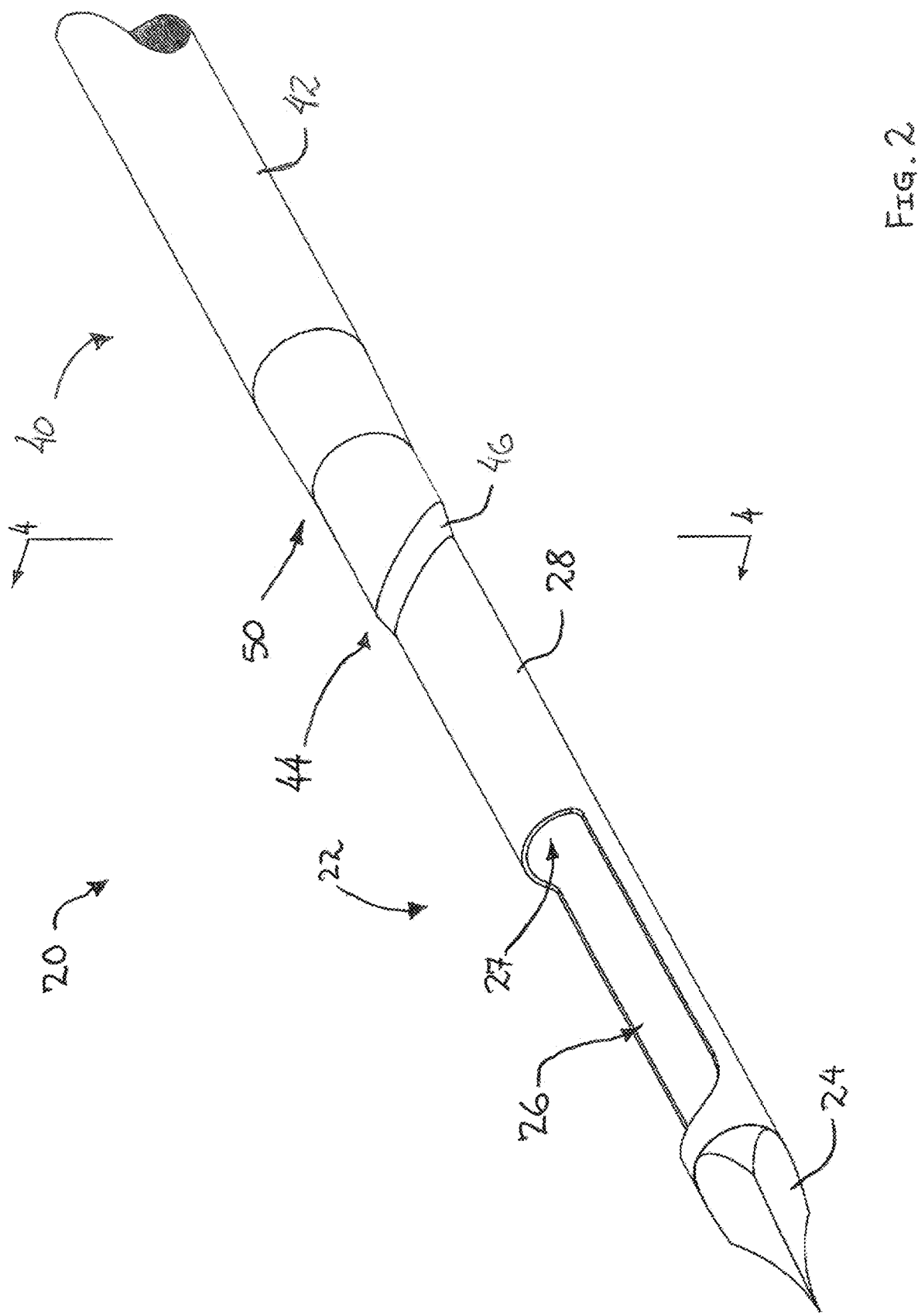
FIG. 2 depicts a detailed perspective view of a needle assembly of the biopsy device of FIG. 1.

FIGS. 2 through 5 show needle assembly (20) in greater detail. As can be seen in FIG. 2, needle assembly (20) comprises an elongate piercer (22) and an elongate cutter (40). As will be described in greater detail below, piercer (22) is generally movable relative to cutter (40) to pierce tissue and collect tissue samples, while cutter is generally movable relative to piercer (22) to sever tissue samples. Piercer (22) comprises a generally hollow cylindrical cannula (28) having a sharp distal tip (24) and a lateral aperture (26) disposed adjacent to distal tip (24). Cannula (28) defines a lumen (27) extending through the length of piercer (22). As will be described in greater detail below, distal tip (24) is generally configured to penetrate tissue of a patient. As will also be described in greater detail below, lateral aperture (26) is generally configured to receive tissue therein such that a tissue sample may be collected within lateral aperture (26) and transported proximally through lumen (27) after the tissue sample is severed by cutter (40).

Cutter (40) comprises an elongate cannula (42) defining an internal lumen (48), a distal end (44) and a swaged portion (50) proximate to the distal end (44). Distal end (44) includes a tapered edge (46) that is generally sharpened to aid in cutting tissue. Tapered edge (46) is oriented at an angle relative to the longitudinal axis of cannula (42). In the present example, tapered edge (46) is oriented such that the leading edge is positioned at the top of cannula (42), while the trailing edge is oriented at the bottom of cannula (42). As best seen in FIGS. 3 and 4, this corresponds to the leading edge of tapered edge (46) being in line with lateral aperture (26) of piercer (22). In some examples, this positioning of the leading edge of tapered edge (46) can aid in the severing of tissue.

Figure 5:
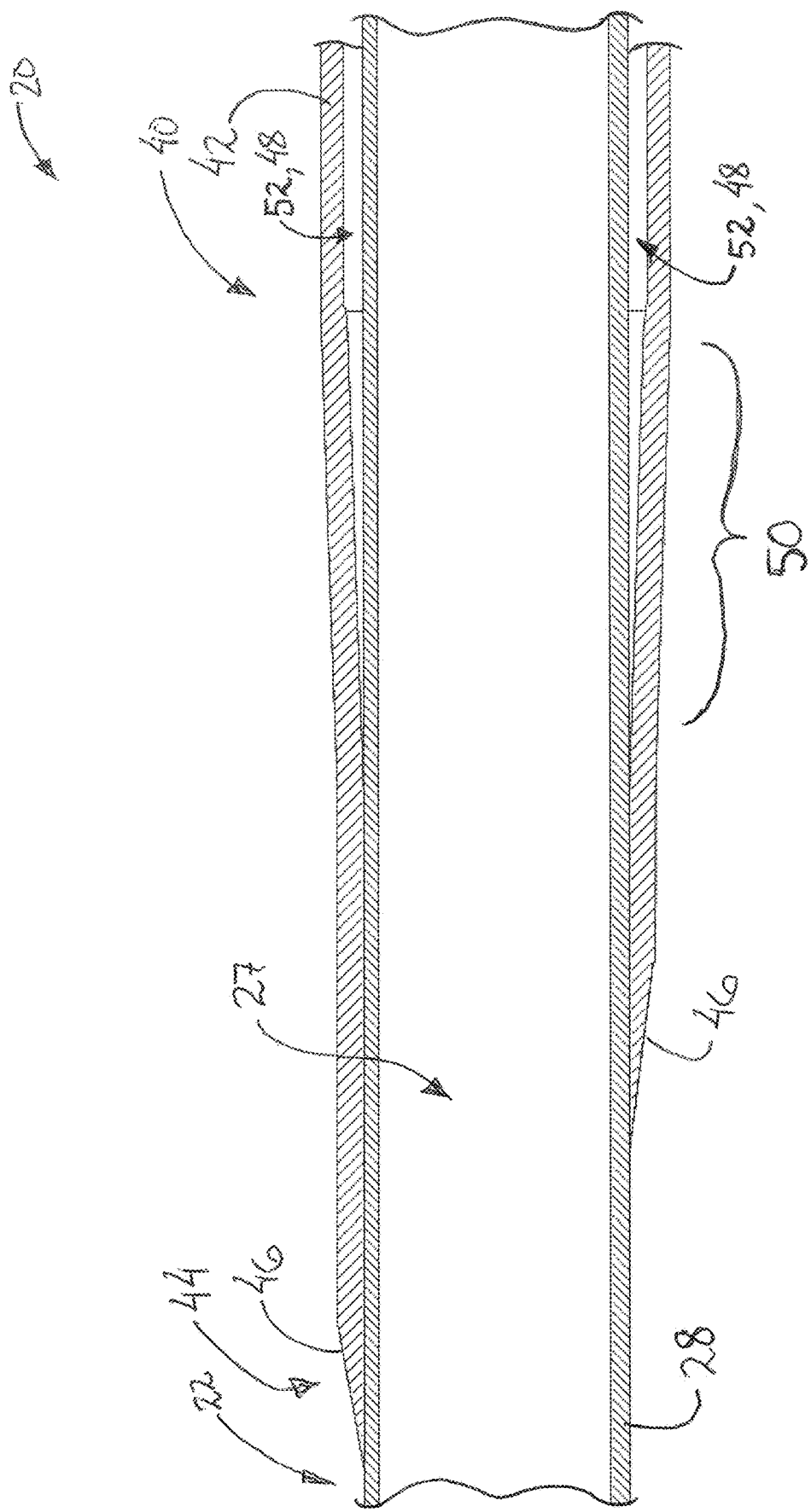
FIG. 5 depicts a detailed side cross-sectional view of the needle assembly of FIG. 2, the cross-section taken along line 4-4 of FIG. 2.

Swaged portion (50) is generally defined by a tapering or necking down of the diameter of cannula (42) just proximally of distal end (44). As best seen in FIG. 5, swaged portion (50) is formed by a continuous change in the diameter of cannula (42) as cannula (42) extends distally. As can be seen, the area of cannula (42) oriented proximally relative to swaged portion (50) defines an inner diameter that is generally greater than the outer diameter of cannula (28) of piercer (22). The difference in the inner diameter of cannula (42) and the outer diameter of cannula (28) forms a gap (52) between cannula (42) and cannula (28). This gap (52) extends proximally from swaged portion (50) along the entire length of cannula (42).

As will be described in greater detail below, gap (52) is generally configured to provide communication of atmospheric air through cannula (42) to aid in the transport of tissue samples through piercer (22). Thus, it should be understood that the particular size of gap (52) can depend on a variety of factors such as the size of tissue samples collected, the pressure of vacuum used to transport tissue samples, the speed of transport, and/or etc. By extension, it should therefore be understood that the difference between the inner diameter of cannula (42) and the outer diameter of cannula (28) can likewise be varied by similar factors.

As can be seen in FIG. 5, swaged portion (50) substantially eliminates gap (52) by a reduction in the diameter of cannula (42). In particular, at the beginning of swaged portion (50), the diameter of cannula (42) is equivalent to the outer diameter of cannula (28) plus the amount of diameter desired to form gap (52). As cannula (42) continues to extend distally through swaged portion (50), the diameter of cannula (42) decreases continuously. In the present example, wagged portion (50) involves the inner diameter of cannula (42) necking down to a diameter that is approximately equivalent to the outer diameter of cannula (28) of piercer (22). Thus, at the distal end of swaged portion (50), gap (52) is substantially eliminated through direct contact between the inner diameter of cannula (42) and the outer diameter of cannula (28). It should be understood that the particular fit between cannula (42) and cannula (28) at distal end (44) of cannula (42) can be varied in view of a variety of factors. For instance, in some examples, the fit can be tight enough to substantially seal gap (52) relative to distal end (44) while still permitting cannula (42) to translate relative to cannula (28). In some examples, this fit can be desirable to prevent leakage of atmospheric air into a patient through gap (52). Of course, various alternative fits can be used as will be apparent to those of ordinary skill in the art in view of the teachings herein.

Later in this application specific means and ways to move needle assembly (20) forward and backwards within core needle biopsy device (10) are described. At this point Applicants wish to point out that although they have included specific ways and means to move needle assembly (20) forwards and backwards, they believe, without intending to be bound thereby, that there are many alternative ways to move needle assembly (20) backwards and forwards and these alternative ways should be known to people of ordinary skill in the art of designing biopsy devices.

Figure 6:
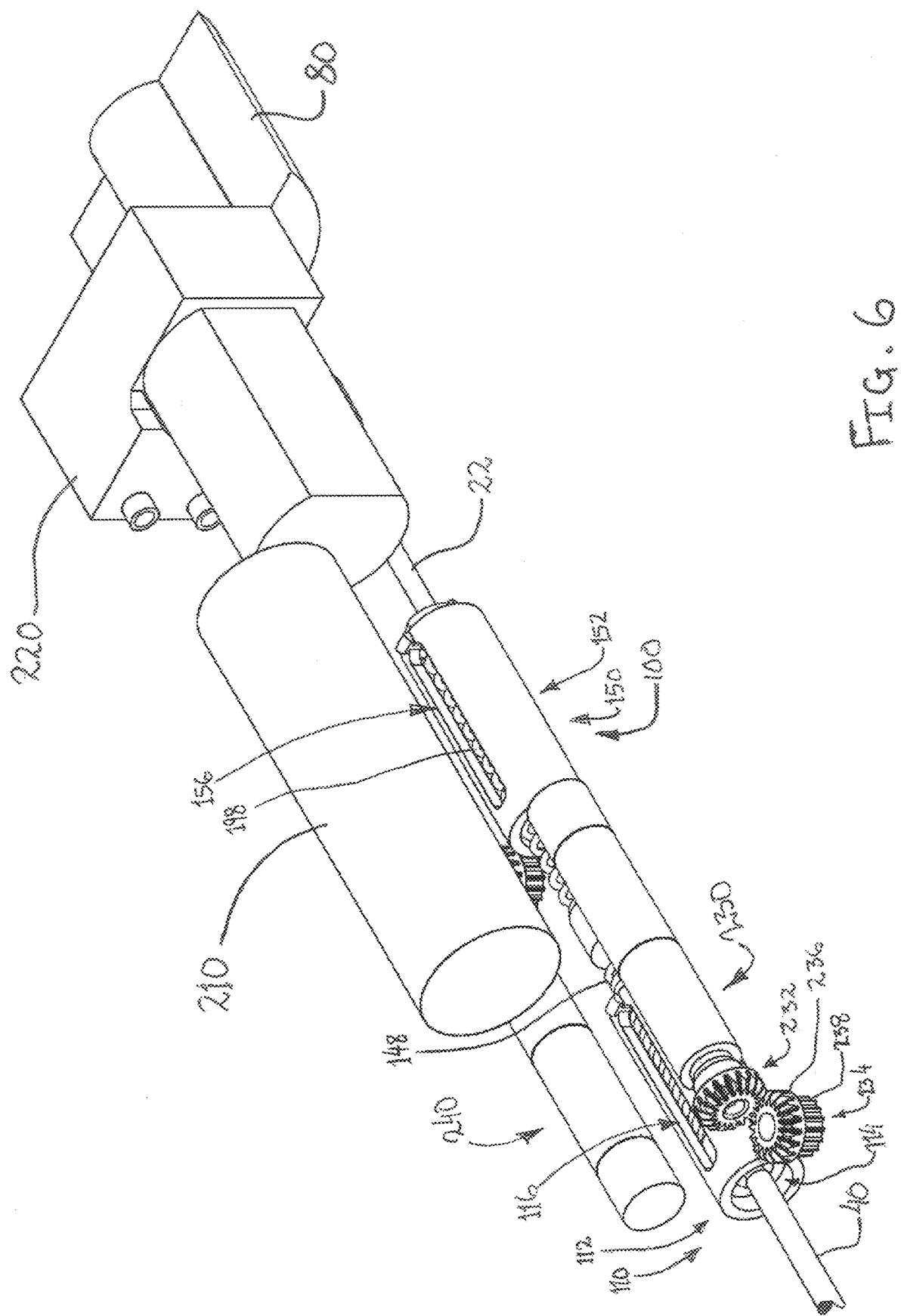
FIG. 6 depicts a perspective view of internal components of the biopsy device of FIG. 1.
Figure 7:
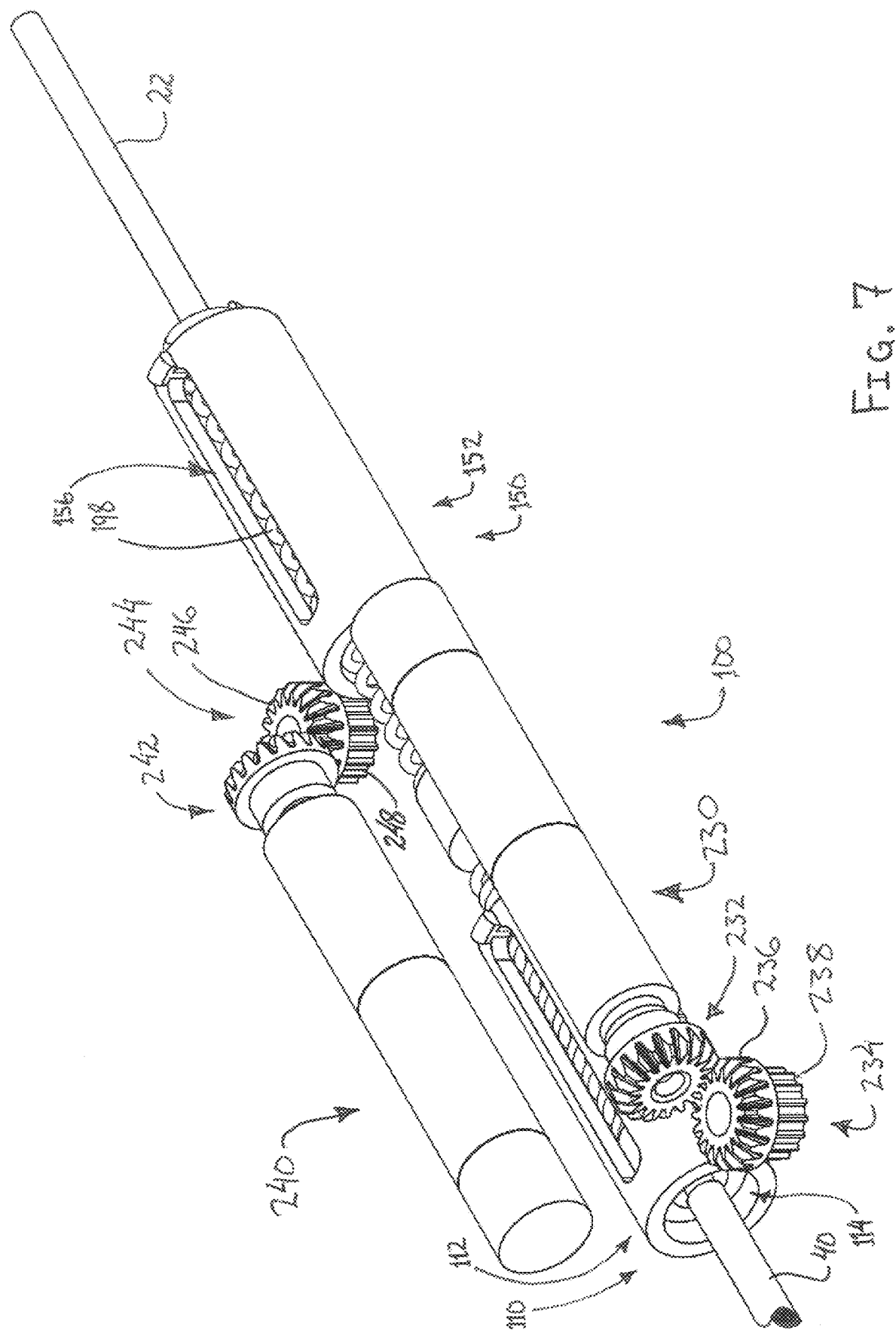
FIG. 7 depicts a perspective view a drive assembly of the biopsy device of FIG. 1.

FIGS. 6 and 7 show various components that can be included within body (12) to control operation of biopsy device (10). As can be seen, the interior of body (12) includes one or more batteries (210), a vacuum pump (220), motors (230, 240), and a drive assembly (100). In the present example, batteries (210), vacuum pump (220), and motors (230, 240) are generally disposed within holster housing (14). Meanwhile, drive assembly (100) is disposed within probe housing (16). Thus, it should be understood that batteries (210), vacuum pump (220), and motors (230, 240) are generally configured to be reusable, while drive assembly (100) is generally configured to be disposable. Additionally, it should be understood that with all these components disposed within body (12), biopsy device (10) is configured as a self-contained tetherless biopsy device, in other examples various components can be disposed remotely relative to body (12). For instance, in some examples batteries (210) can be omitted in favor of a tethered power supply. Similarly, vacuum pump (220) can also be omitted in favor of an external vacuum source. Motors (230, 240) may likewise be omitted in favor of a remote power source in communication with body (12) by a rotary drive cable. Of course, various alternative configuration will be apparent to those of ordinary skill in the art in view of the teachings herein.

Figure 8:
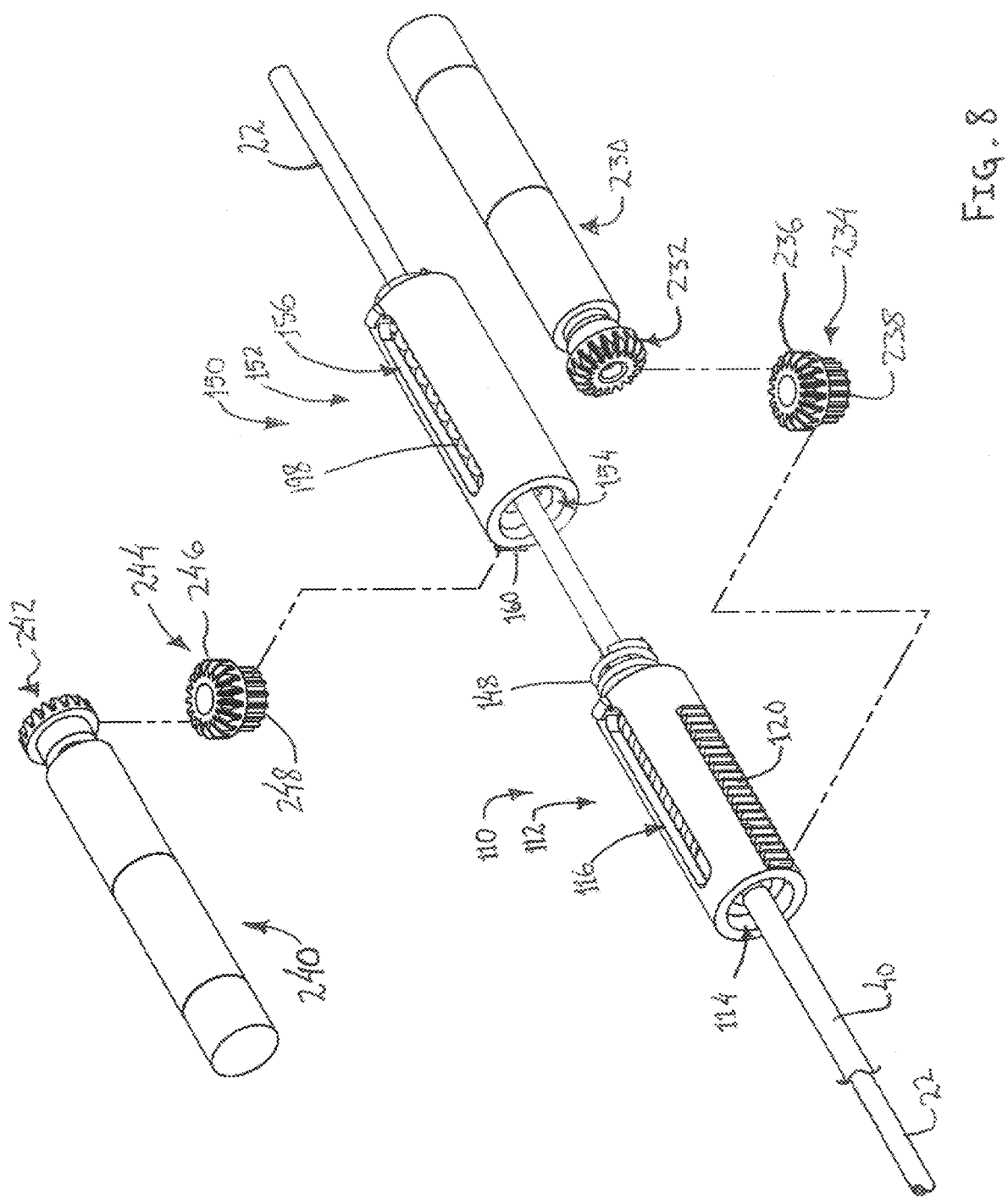
FIG. 8 depicts a perspective partially exploded view of the drive assembly of FIG. 7.

FIGS. 7 and 8 show motors (230, 240) in greater detail below. As will be understood, motors (230, 240) are generally configured to translate at least a portion of drive assembly (100) to cock or otherwise prepare cutter (40) and piercer (22) for firing. As can be seen, motors (230, 240) comprise a cutter motor (230) and a piercer motor (240). Cutter motor (230) is generally configured to translate a portion of drive assembly (100) to thereby translate cutter (40). In particular, cutter motor (230) is coupled to a bevel gear (232), which is configured to mesh with a combination gear (234). Combination gear (234) includes both a bevel gear portion (236) and a spur gear portion (238). As will be described in greater detail below, bevel gear (234) is configured to be driven by cutter motor (230) to rotate combination gear (234). Combination gear (234) is then configured to mesh with at least a portion of drive assembly (100) to drive a rack or similar feature to translate cutter (40) from a fired position to a cocked position.

Piercer motor (240) is generally configured to translate a portion of drive assembly to thereby translate piercer (22). In particular, piercer motor (240) is coupled to a bevel gear (242), which is configured to mesh with a combination gear (244). Combination gear (244) includes both a bevel gear portion (246) and a spur gear portion (248). As will be described in greater detail below, bevel gear (244) is configured to be driven by piercer motor (240) to rotate combination gear (244). Combination gear (244) is then configured to mesh with at least a portion of drive assembly (100) to drive a rack or similar feature to translate piercer (22) from a fired position to a cocked position.

Figure 9:
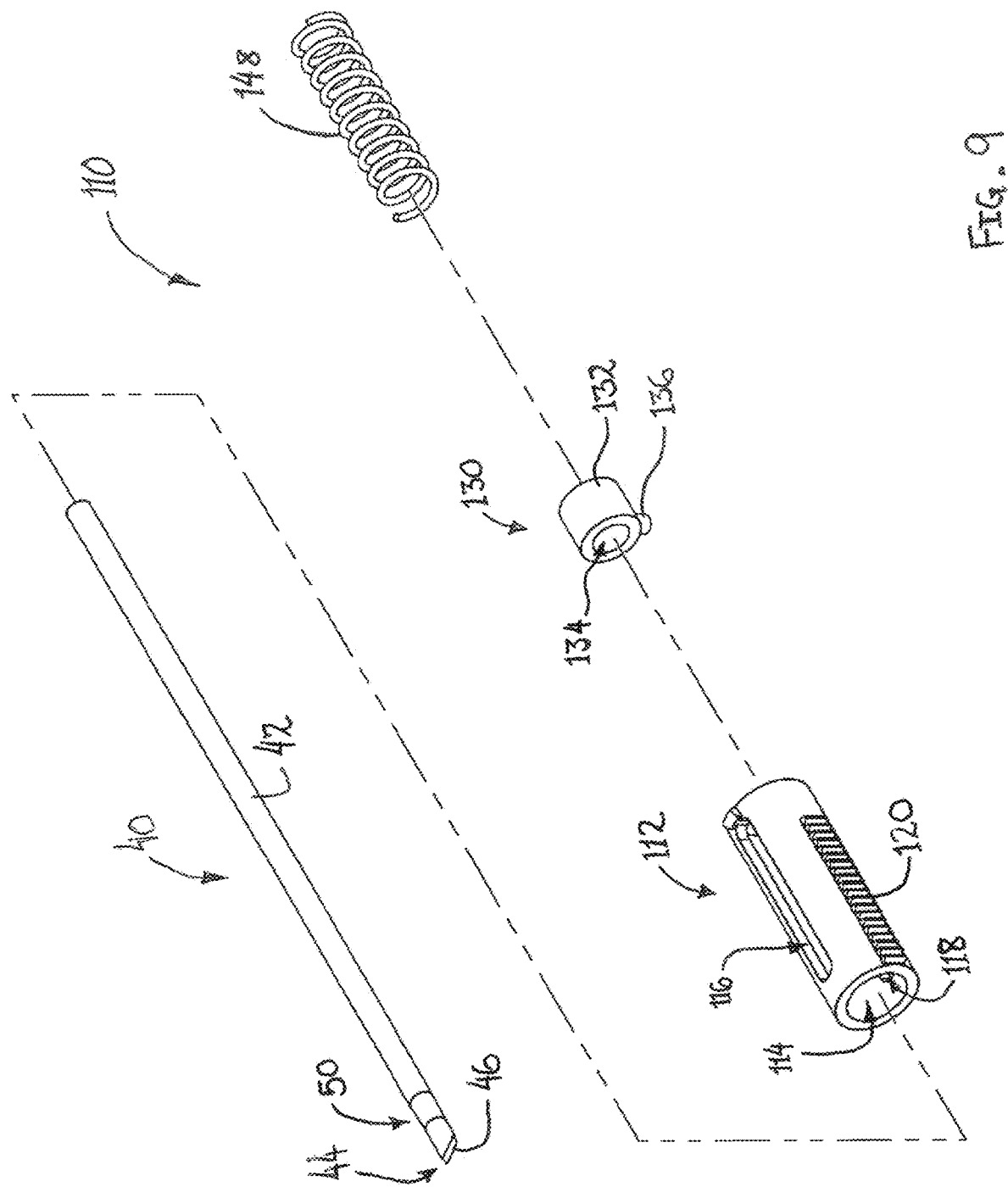
FIG. 9 depicts a perspective exploded view of a cutter drive of the drive assembly of FIG. 7.

Drive assembly (100) includes a cutter drive (110) and a piercer drive (150). As best seen in FIG. 9, cutter drive (110) includes a manipulator (112), a cutter driver (130), and a coil spring (148). As will be described in greater detail below, manipulator (112) is generally configured to manipulate cutter driver (130) into a cocked position, while coil spring (148) is generally configured to fire cutter (40) distally via cutter driver (130). Manipulator (112) defines a hollow interior (114) and includes an upper channel (116), a lower channel (118) and a rack (120). Hollow interior (114) is configured to receive the combination of cutter (40) and cutter driver (130).

Upper and lower channels (116, 118) are configured to permit at least a portion of cutter driver (130) to extend outside of the outer diameter defined by manipulator (112). In the present example, only lower channel (118) is used in this way. However, the presence of upper channel (116) makes manipulator (112) generally symmetrical so that manipulator (112) can be used in other positions. For instance, in some examples manipulator (112) can be positioned so that rack (120) is facing into the page in FIG. 9 as opposed to out of the page. As will be understood, this configuration can permit manipulator (112) to be used interchangeably with a corresponding component of piercer driver (150).

Rack (120) is configured to mesh with spur gear portion (238) of combination gear (234). As will be described in greater detail below, this configuration permits cutter motor (230) to rotate and drive linear translation of manipulator (112). In some circumstances, this linear translation of manipulator (112) can be used to manipulate cutter driver (130) along with cutter (40) to a cocked position where coil spring (148) is loaded to fire cutter (40).

Cutter driver (130) includes a cylindrical body (132) defining a cutter bore (134) and a catch post (136) extending downwardly from cylindrical body (132). Cylindrical body (132) is sized in general correspondence with the diameter of coil spring (148). This relationship between the size of cylindrical body (132) and coil spring (148) permits coil spring (148) to transfer energy to cylindrical body (132) to thereby drive firing of cutter (40).

Cutter bore (134) is sized to receive cutter (40) therein. When cutter drive (110) is fully assembled, cutter bore (134) is coaxial with cutter (40). Additionally, cylindrical body (132) is generally fixedly secured to cutter (40). In some examples, cutter bore (134) is sized to have an interference fit with cannula (42) of cutter (40) to secure cylindrical body (132) to cutter (40). In other examples, the diameter of cutter bore (134) is slightly oversized relative to the outer diameter of cannula (42) of cutter (40). In such examples, cylindrical body (132) can be secured to cutter (40) by adhesion bonding or the like. In still other examples, cylindrical body (132) can be directly overmolded onto the surface of cannula (42) to secure cylindrical body (132) to cutter (40). Of course, other suitable methods of joining cylindrical body (132) to cutter (40) may be used as will be apparent to those of ordinary skill in the art in view of the teachings herein.

Catch post (136) extends downwardly from cylindrical body (132). As will be described in greater detail below, catch post (136) is generally configured to permit cylindrical body (132) to be held against the resilient bias of spring (148). Catch post (136) extends away from cylindrical body (132) for a length sufficient for catch post (136) to protrude from lower channel (118) of manipulator (112). As will be described in greater detail below, this extension permits at least a portion of probe housing (16) to engage catch post (136) and thereby maintain cylindrical body (132) in the cocked position against the resilient bias of coil spring (148).

Figure 10:
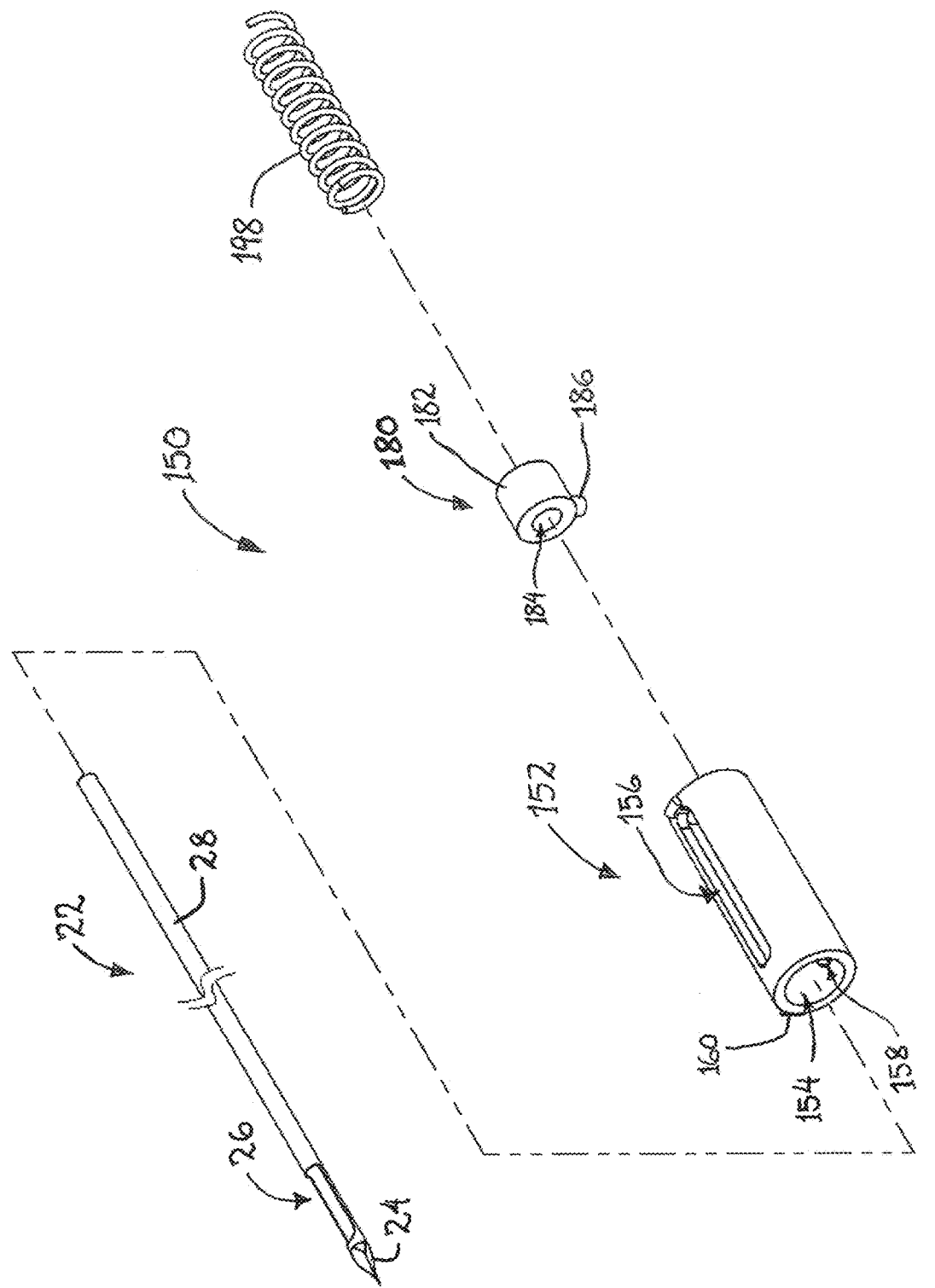
FIG. 10 depicts a perspective exploded view of a piercer drive of the drive assembly of FIG. 7.

As best seen in FIG. 10, piercer drive (150) includes a manipulator (152), a piercer driver (180), and a coil spring (198). As will be described in greater detail below, manipulator (152) is generally configured to manipulate piercer driver (180) into a cocked position, while coil spring (198) is generally configured to fire piercer (22) distally via piercer driver (180). Manipulator (152) defines a hollow interior (154) and includes an upper channel (156), a lower channel (158) and a rack (160). Hollow interior (154) is configured to receive the combination of piercer (22) and piercer driver (180).

Upper and lower channels (156, 158) are configured to permit at least a portion of piercer driver (180) to extend outside of the outer diameter defined by manipulator (152). In the present example, only lower channel (158) is used in this way. However, the presence of upper channel (156) makes manipulator (152) generally symmetrical so that manipulator (152) can be used in other positions. For instance, in some examples manipulator (152) can be positioned so that rack (160) is facing out of the page in FIG. 10 as opposed to into the page. As will be understood, this configuration can permit manipulator (152) to be used interchangeably with manipulator (112) described above.

Rack (160) is configured to mesh with spur gear portion (248) of combination gear (244). As will be described in greater detail below, this configuration permits piercer motor (240) to rotate and drive linear translation of manipulator (152). In some circumstances, this linear translation of manipulator (152) can be used to manipulate piercer driver (180) along with piercer (22) to a cocked position where coil spring (198) is loaded to fire piercer (22).

Piercer driver (180) includes a cylindrical body (182) defining a piercer bore (184) and a catch post (186) extending downwardly from cylindrical body (182). Cylindrical body (182) is sized in general correspondence with the diameter of coil spring (198). This relationship between the size of cylindrical body (182) and coil spring (198) permits coil spring (198) to transfer energy to cylindrical body (182) to thereby drive firing of piercer (22).

Piercer bore (184) is sized to receive piercer (22) therein. When piercer drive (150) is fully assembled, piercer bore (184) is coaxial with piercer (22). Additionally, cylindrical body (182) is generally fixedly secured to piercer (22). In some examples, piercer bore (184) is sized to have an interference fit with cannula (28) of piercer (22) to secure cylindrical body (182) to piercer (22). In other examples, the diameter of piercer bore (184) is slightly oversized relative to the outer diameter of cannula (28) of piercer (22). In such examples, cylindrical body (182) can be secured to piercer (22) by adhesion bonding or the like. In still other examples, cylindrical body (182) can be directly overmolded onto the surface of cannula (28) to secure cylindrical body (182) to piercer (22). Of course, other suitable methods of joining cylindrical body (182) to piercer (22) may be used as will be apparent to those of ordinary skill in the art in view of the teachings herein.

Catch post (186) extends downwardly from cylindrical body (182). As will be described in greater detail below, catch post (186) is generally configured to permit cylindrical body (182) to be held against the resilient bias of spring (198). Catch post (186) extends away from cylindrical body (182) for a length sufficient for catch post (186) to protrude from lower channel (158) of manipulator (152). As will be described in greater detail below, this extension permits at least a portion of probe housing (16) to engage catch post (186) and thereby maintain cylindrical body (182) in the cocked position against the resilient bias of coil spring (198).

Figure 11A:
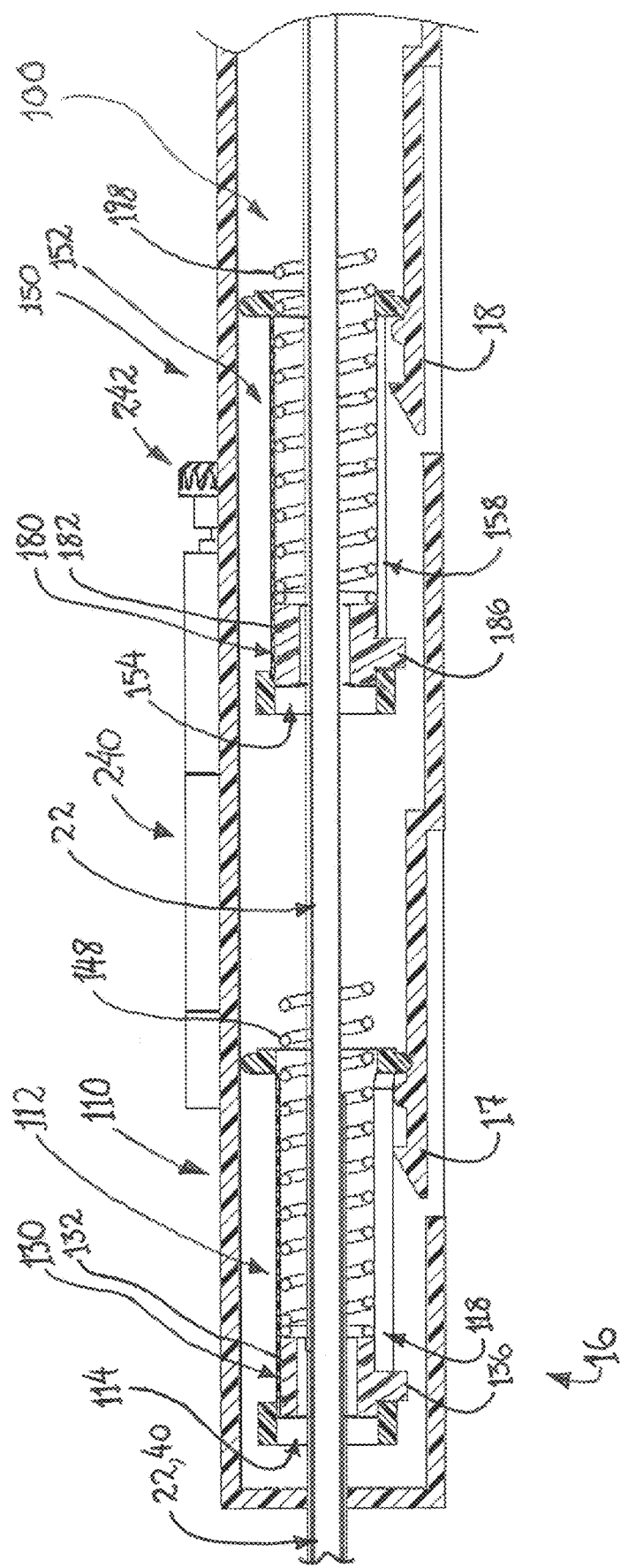
FIG. 11A depicts a side cross-sectional view of the biopsy device of FIG. 1, with the cross-section taken along line 11-11 of FIG. 1 and the drive assembly of FIG. 7 in an initial position.

FIGS. 11A through 12C show an exemplary use of biopsy device (10) to collect one or more tissue samples from a patient, using a single insertion of needle assembly (20). In particular, FIGS. 11A through 11E show the internal operation of biopsy device (10) in detail. As is best seen in FIG. 11A, biopsy device (10) is initially in a fired or initial position. In this position, both piercer (22) and cutter (40) are positioned in a distal-most position corresponding to the position of piercer (22) and cutter (40) after firing. When piercer (22) and cutter (40) are both in the fired or initial position, manipulators (112, 152), piercer driver (180), and cutter driver (130) are all in a distal-most position. Coil springs (148, 198) are also in an uncompressed position.

In preparation for inserting needle assembly (20) into a patient, it can be desirable to first cock needle assembly (20) to permit firing of needle assembly (20) into a suspicious lesion. To cock needle assembly (20), both cutter motor (230) and piercer motor (240) are activated. This causes bevel gears (232, 242) to rotate. Rotation of bevel gears (232, 242) then results in rotation of combination gears (234, 244). Engagement between a spur gear portion (238, 248) of each combination gear (234, 244) and a respective rack (120, 160) causes each manipulator (112, 152) to translate. Manipulators (112, 152) are thus translated proximally by motors (230, 240) from the position shown in FIG. 11A to the position shown in FIG. 11B.

As manipulators (112, 152) are translated proximally, cutter driver (130) and piercer driver (150) are likewise translated proximally by contact between each respective catch post (136, 186) and the distal end of each lower channel (118, 158). Proximal translation of cutter driver (130) and piercer driver (150) causes each coil spring (148, 198) to compress in proportion to the translation. Although not shown, it should be understood that in the present example the interior of probe housing (16) can includes a stop or other geometric feature to provide a mechanical ground for the proximal end of each coil spring (148, 198) to permit compression of each coil spring (148, 198).

Figure 11B:
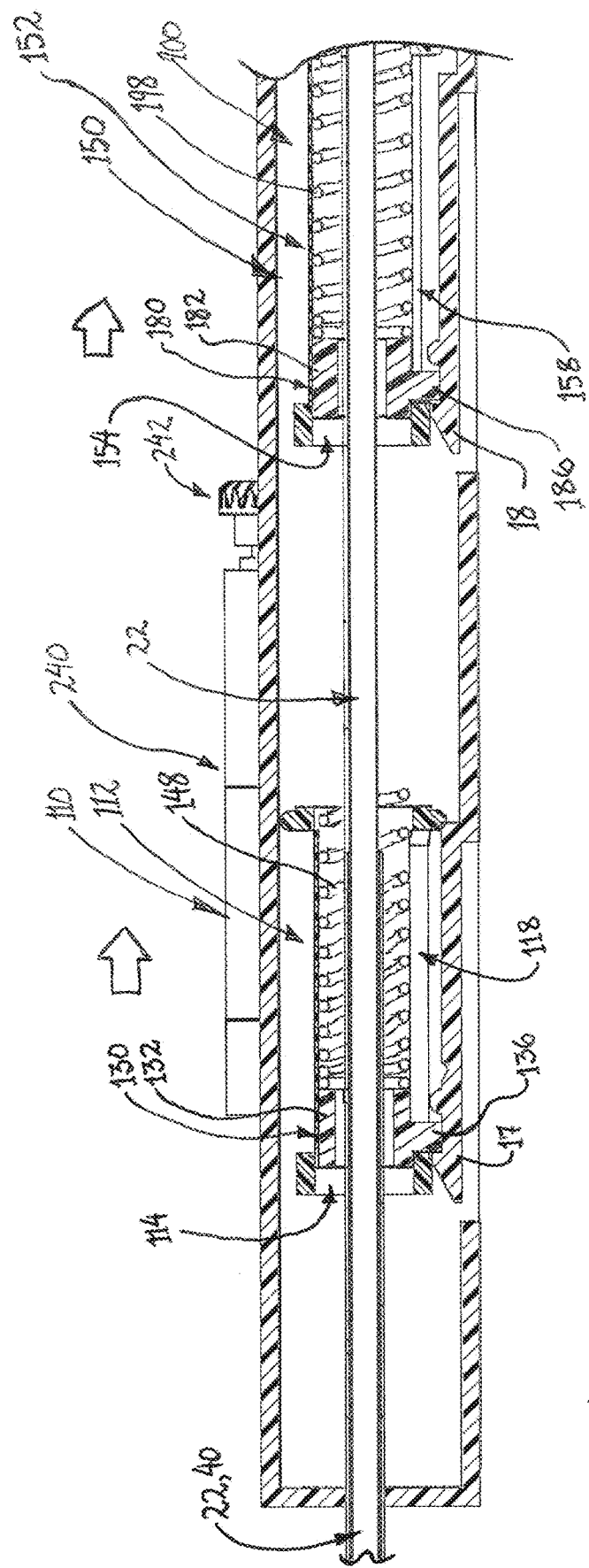
FIG. 11B depicts another cross-sectional view of the biopsy device of FIG. 1, with the drive assembly of FIG. 7 in a cocked position.

Once drive assembly (100) is positioned as shown in FIG. 11B, a portion of probe housing (16) fastens to cutter driver (130) and piercer driver (180). In particular, in the present example probe housing (16) is shown as having resiliently biased latches (17, 18). For instance, a distal latch (17) is configured to selectively couple to catch post (136) of cutter driver (130) to selectively hold cutter driver (130) in the cocked position. Similarly, a proximal latch (18) is configured to selectively couple to catch post (186) of piercer driver (180) to selectively hold piercer driver (180) in the cocked position. Each latch (17, 18) of the present example is integral with probe housing (16) and includes a tooth protruding from a resilient arm. Thus, each latch (17, 18) is generally movable to flex into and out of engagement with cutter driver (130) and piercer driver (180), respectively.

Although the probe housing (16) of the present example includes latches (17, 18), it should be understood that in other examples the same functionality can be accomplished in a variety of ways. For instance, in some examples latches (17, 18) can be replaced with a solenoid or other electromechanical device to selectively hold cutter driver (130) and piercer driver (180) in the cocked position. In other examples, latches (17, 18) can be in the form of other alternative configurations both integral with probe body (16) or configured as a separate component. In all such alternative examples, it should be understood that latches (17, 18) or any other actuator can be connected with each other to promote firing of cutter (40) and piercer (22) in a predetermined sequence. Of course, other alternative configurations will be apparent to those of ordinary skill in the art in view of the teachings herein.

Once drive assembly (100) is cocked as shown in FIG. 11B, potential energy is stored in coil springs (148, 198) such that cutter (40) and piercer (22) are both ready to be fired distally upon release of the potential energy stored in coil springs (148, 198). To release this potential energy, latches (17, 18) can be actuated to disengage cutter driver (130) and piercer driver (180). However, prior to disengaging cutter driver (130) and piercer driver (180) it may be desirable to advance manipulators (112, 152). For instance, in the position shown in FIG. 11B, manipulators (112, 152) are positioned proximally after driving cuter driver (130) and piercer driver (180) proximally. In some uses, it may be desirable to advance manipulators (112, 152) distally ahead of firing to avoid the possibility of manipulators (112, 152) impeding the firing of cutter (40) and piercer (22). To advance manipulators (112, 152) distally, the rotation of cutter motor (230) and piercer motor (240) is reversed until manipulators (112, 152) are positioned as shown in FIG. 11C.

Figure 11C:
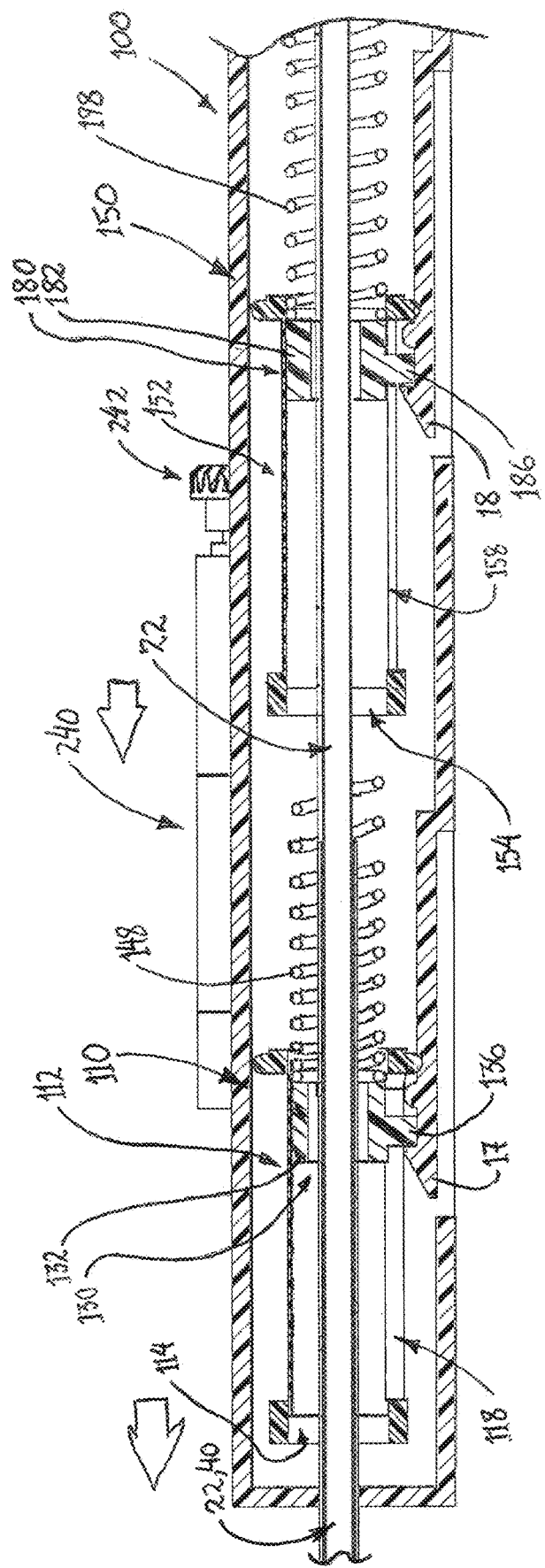
FIG. 11C depicts still another cross-sectional view of the biopsy device of FIG. 1, with the drive assembly of FIG. 7 in a ready position.
Figure 11D:
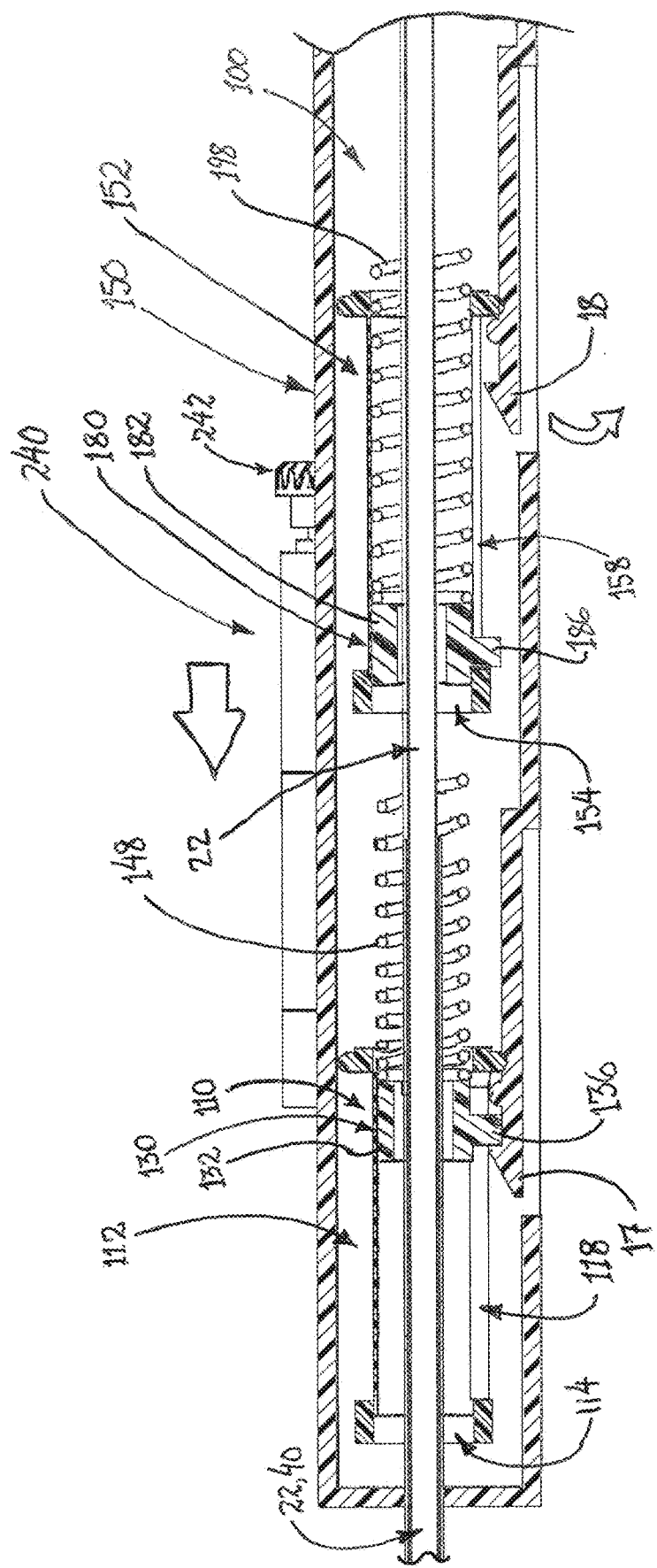
FIG. 11D depicts yet another cross-sectional view of the biopsy device of FIG. 1, with the drive assembly of FIG. 7 in a partially fired position.

Once manipulators (112, 152) are positioned as shown in FIG. 11C, drive assembly (100) is prepared for firing. In the present use, piercer (22) is fired first to penetrate a suspicious lesion. Piercer (22) is fired by actuating proximal latch (18) as shown in FIG. 11D. Actuation of proximal latch (18) results in disengagement of proximal latch (18) with catch post (186) of piercer driver (180). With catch post (186) disengaged, piercer driver (180) is free to translate distally using energy supplied by coil spring (198). Since piercer driver (180) is fixedly secured to piercer (22), piercer (22) likewise translates distally.

Figure 12B:
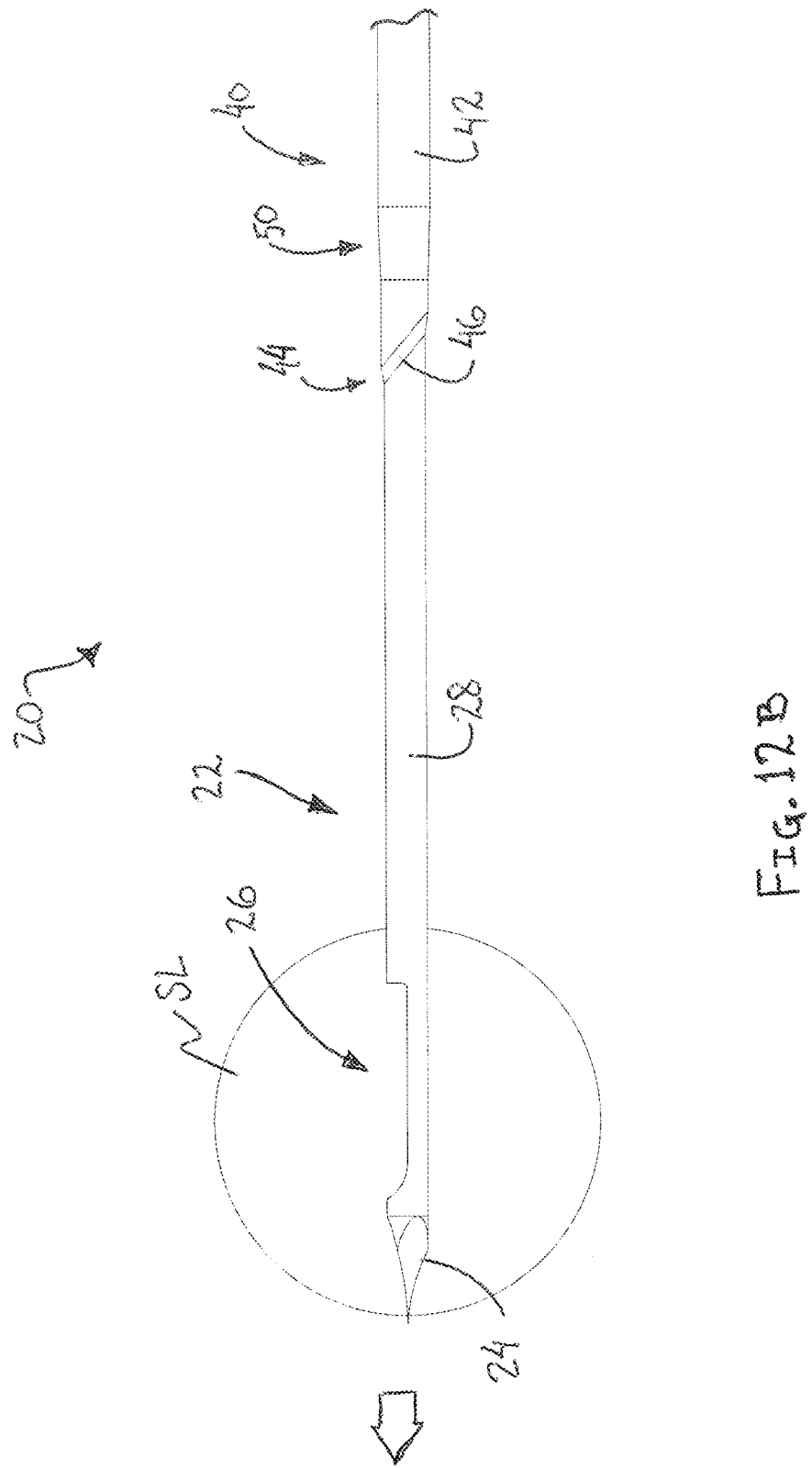
FIG. 12B depicts another side elevational view of the needle assembly of FIG. 2, with a piercer of the needle assembly fired into the suspicious lesion.

The firing of piercer (22) that results from the actuator shown in FIG. 11D can be seen by comparing FIGS. 12A and 12B. As can be seen, piercer (22) is initially positioned proximate to a suspicious lesion (SL) as shown in FIG. 12A. Once piercer (22) is fired as described above, piercer (22) advances distally into the suspicious lesion (SL) as shown in FIG. 12B. It should be understood that this movement of piercer (22) can result in minimal displacement of the suspicious lesion (SL), thereby avoiding migration of the suspicious lesion (SL) and enhancing the quality of any collected tissue samples.

After piercer (22) is fired into the suspicious lesion (SL), it may be desirable to acquire a tissue sample by advancing cutter (40) relative to piercer (22). In particular, once piercer (22) is fired into the suspicious lesion (SL), tissue can prolapse into lateral aperture (26) of piercer (22). In some uses, the prolapse of tissue into lateral aperture (26) may occur through internal tension within the tissue. In other uses, vacuum can be applied to lumen (27) of piercer (22) to provide a force to assist with prolapsing tissue into lateral aperture (26).

Figure 11E:
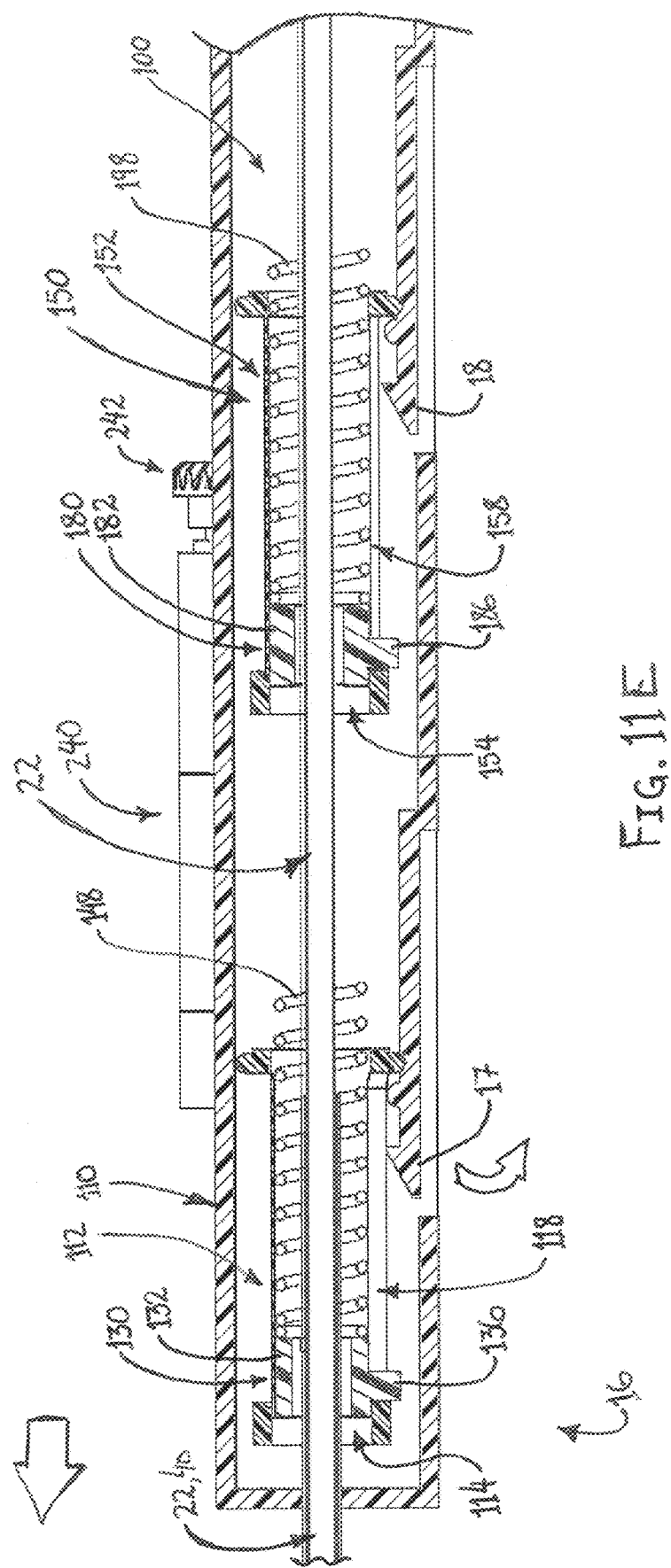
FIG. 11E depicts yet another cross-sectional view of the biopsy device of FIG. 1, with the drive assembly of FIG. 7 in a fully fired position.

Once tissue is prolapsed into lateral aperture (26) of piercer (22), a tissue sample can be severed using cutter (40). In particular, cutter (40) can be fired by first actuating distal latch (17) as shown in FIG. 11E. Actuation of distal latch (17) disengages catch post (136) of cutter driver (130). Disengagement of catch post (136) permits cutter driver (130) to freely translate distally. Accordingly, upon disengagement of catch post (136), cutter driver (130) will fire distally by energy provided by coil spring (148). Since cutter driver (130) is fixedly secured to cutter (40), cutter (40) will likewise fire distally into the position shown in FIGS. 11E and 12C.

Figure 12C:
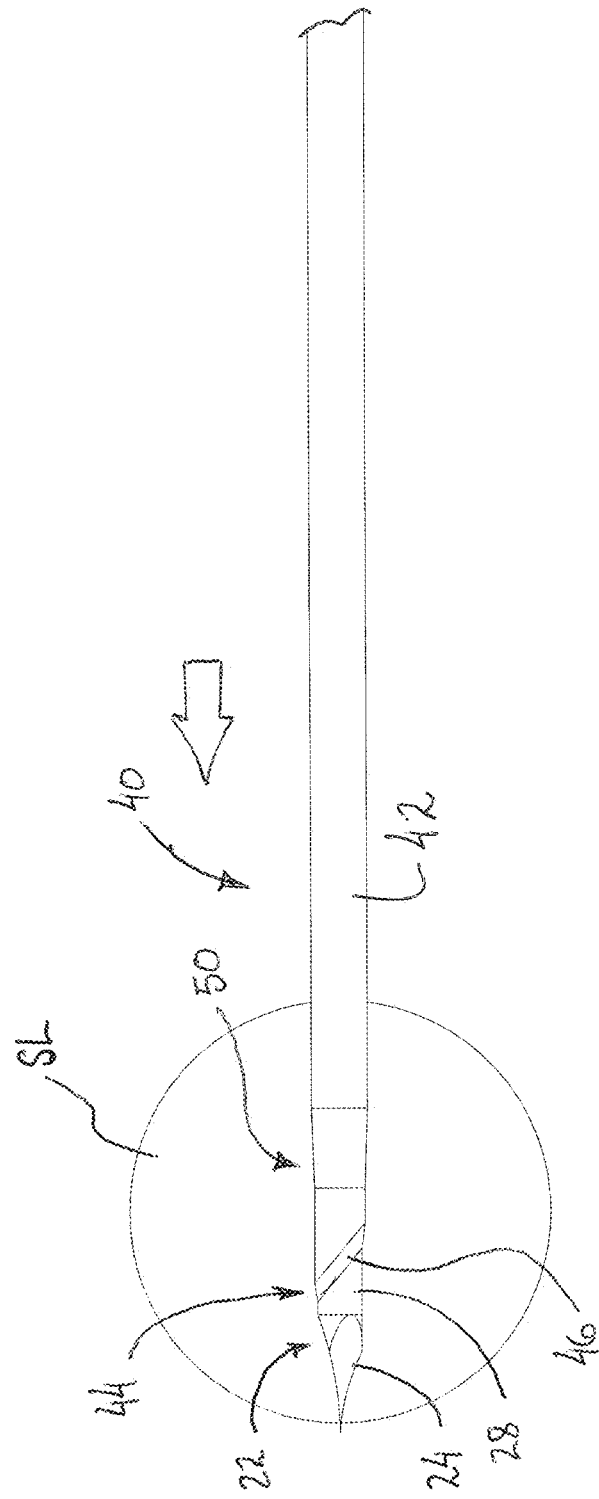
FIG. 12C depicts still another side elevational view of the needle assembly of FIG. 2, with a cutter of the needle assembly fired into the suspicious lesion.

The firing of cutter (40) that results from the actuation shown in FIG. 11E can be seen by comparing FIGS. 12B and 12C. As can be seen, cutter (40) is initially positioned proximate to the suspicious lesion (SL) immediately before firing, as shown in FIG. 12B. Once cutter (40) is fired, distal end (44) is translated distally past lateral aperture (26) of piercer (22), as shown in FIG. 12C. As distal end (44) passes lateral aperture (26), the tissue sample is severed.

Next it may be desirable to transport the severed tissue sample through lumen (27) of piercer (22) and into tissue sample holder (80). To transport the severed tissue sample, a vacuum is applied to lumen (27) of piercer (22). Such vacuum can be supplied by way of tissue sample holder (80) to urge the severed tissue sample into tissue sample holder (80). As vacuum is applied, a proximal force will build on the proximal end of the severed tissue sample. Once the proximal force is sufficiently large, the severed tissue sample will begin to move proximally through lumen (27) of piercer (22). However, movement of the severed tissue sample can cause negative pressure to build in the distal end of the severed tissue sample. Accordingly, it may be desirable to also supply either atmospheric air or back pressure to the distal end of the severed tissue sample. Such atmospheric air or back pressure is supplied in the present example by gap (52) that is defined by cutter (40). In the present example, atmospheric air is supplied continuously through lumen (48) by way of the proximal end of cutter (40). However, it should be understood that in other examples valving or other fluid control mechanisms can be used to regulate the supply of atmosphere.

Although atmosphere is supplied continuously to cutter (40), it should be understood that atmosphere is only selectively supplied to piercer (22) by cutter (40). For instance, after a tissue sample is severed, gap (52) of cutter (40) is positioned such that gap (52) is in fluid communication with lateral aperture (26). Thus, atmospheric air can flow freely from cutter (40) and into piercer (22). However, when distal end (44) of cutter (40) is positioned proximally relative to lateral aperture (26), lateral aperture (26) is not in fluid communication with gap (52) and flow of atmospheric air to lateral aperture (26) is prevented.

Once the severed tissue sample has been transported to tissue sample holder (80), it may be desirable to collect one or more additional tissue samples. To collect additional tissue samples, cutter (40) and piercer (22) are both retracted using motors (230, 240). This retraction also cocks both cutter (40) and piercer (22) so that the same tissue sample collection process described above can be repeated until a desired number of tissue samples are collected or tissue sample holder (80) is filled.

Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A core needle biopsy device, comprising: a needle assembly having a hollow piercer disposed within a hollow cutter, wherein the cutter has a distal tip and a swaged portion proximate to the distal tip; and a drive assembly configured to selectively cock and fire the piercer and the cutter.

Example 2

The core needle biopsy device of Example 1, wherein the swaged portion is tapered to form a gap between the piercer and the cutter proximally of the distal tip of the cutter.

Example 3

The core needle biopsy device of Example 2, wherein the piercer has a sharp tip and a lateral aperture proximate to the sharp tip, wherein the gap defined by the swaged portion of the cutter is configured to supply atmospheric air to the lateral aperture of the piercer when the distal tip is disposed proximally relative to the lateral aperture.

Example 4

The core needle biopsy device of any one or more of Examples 1 through 3, wherein the distal tip of the cutter forms a tapered edge configured to cut tissue.

Example 5

The core needle biopsy device of Example 4, wherein the tapered edge of the cutter is oriented at an oblique angle relative to a longitudinal axis defined by the cutter.

Example 6

The core needle biopsy device of any one or more of Examples 1 through 5, wherein the piercer is configured to transport tissue samples through a lumen defined by the piercer to a tissue sample holder associated with the core needle biopsy device.

Example 7

The core needle biopsy device of any one or more of Examples 1 through 6, wherein the drive assembly includes a cutter drive and a piercer drive, wherein the cutter drive is configured to cock and fire the cutter, wherein the piercer drive is configured to cock and fire the piercer.

Example 8

The core needle biopsy device of Example 7, wherein the cutter drive and the piercer drive are operable independently of each other to cock and fire the cutter and the piercer, respectively.

Example 9

The core needle biopsy device of Example 7, wherein the cutter drive and the piercer drive each include a manipulator, a driver, and a spring, respectively, wherein the manipulator is movable relative to a fixed portion of the spring to move the driver to a cocked position.

Example 10

The core needle biopsy device of Example 9, wherein each manipulator includes a rack, wherein the rack is configured to be driven by a motor to translate each manipulator proximally and distally.

Example 11

A needle assembly for use in a biopsy device, the needle assembly comprising: a hollow piercer having a sharp tip configured to penetrate tissue and a lateral aperture; and a cutter disposed coaxially around the piercer and having a distal cutting edge and a swaged portion proximate to the distal cutting edge.

Example 12

The needle assembly of Example 11, wherein the swaged portion of the cutter is defined by a taper in a diameter of the cutter, wherein the swaged portion is tapered inwardly as the cutter extends distally towards the distal cutting edge.

Example 13

The needle assembly of any one or more of Examples 11 through 12, wherein the piercer defines a lumen extending from the lateral aperture to a proximal end of the piercer.

Example 14

The needle assembly of Example 13, wherein the lumen is configured to communicate tissue samples from the lateral aperture to a tissue sample holder in communication with the proximal end of the piercer.

Example 15

The needle assembly of any one or more of Examples 11 through 14, wherein the swaged portion defines a gap between an interior of the cutter and an exterior of the piercer, wherein the gap extends from the swaged portion to a proximal end of the cutter.

Example 16

The needle assembly of Example 15, wherein the gap defined by the swaged portion is configured to communicate fluid from the proximal end of the cutter to the lateral aperture of the piercer.

Example 17

The needle assembly of Example 16, wherein the proximal end of the cutter is in open fluid communication with atmospheric air.

Example 18

The needle assembly of Example 16, wherein the proximal end of the cutter is in selective fluid communication with atmospheric air.

Example 19

The needle assembly of Example 16, wherein the cutter is movable relative to the piercer such that the cutter is configured to provide selective fluid communication to the lateral aperture of the piercer using the gap defined by the swaged portion.

Example 20

The needle assembly of Example 16, wherein the distal cutting edge of the cutter is configured to fluidly isolate an exterior of the piercer relative to the gap defined by the swaged portion.

Example 21

A method for using a core needle biopsy device to collect multiple tissue samples using a single insertion of a needle assembly, wherein the needle assembly includes a piercer and a cutter disposed coaxially about the piercer, the method comprising: inserting the needle assembly into a patient to position a distal tip of the piercer adjacent to a suspicious lesion; firing the piercer distally to position a lateral aperture of the piercer within at least a portion of the suspicious lesion; firing the cutter distally sever a tissue sample into the lateral aperture of the piercer; and transporting the tissue sample proximally though a lumen defined by the piercer using vacuum applied to a proximal end of the tissue sample.

Example 22

The method of Example 21, wherein the step of firing the cutter includes advancing a cutting edge of the cutter distally past the lateral aperture of the piercer.

Example 23

The method of any one or more of Examples 21 through 22, further comprising retracting the cutter relative to the piercer after transporting the tissue sample in preparation of collecting another tissue sample.

Example 24

The method of any one or more of Examples 23, repeating the steps of inserting the needle assembly, firing the cutter distally, transporting the tissue sample, and retracting the cutter to collect a multiple tissue samples, wherein the steps are repeated while the piercer remains in the patient.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

I claim:

1. A core needle biopsy device, comprising:
   (a) a body;
   (b) a needle assembly extending distally from the body and having a hollow piercer and a hollow cutter, the piercer including a sharp tip and a lateral aperture proximate the sharp tip, the piercer being disposed within the cutter, the cutter having a distal tip and a swaged portion proximate the distal tip, the swaged portion being tapered to form a gap between the piercer and the cutter proximally of the distal tip, the gap defined by the swaged portion of the cutter being in communication with a proximal opening defined by the cutter, the proximal opening and the gap being configured to together supply atmospheric air to the lateral aperture of the piercer when the distal tip of the cutter is disposed distally relative to the lateral aperture; and
   (b) a drive assembly configured to selectively cock and fire the piercer and the cutter relative to the body.

2. The core needle biopsy device of claim 1, the distal tip of the cutter being configured to fluidly isolate an exterior of the piercer relative to the gap defined by the swaged portion.

3. The core needle biopsy device of claim 1, the distal tip of the cutter forming a tapered edge configured to cut tissue.

4. The core needle biopsy device of claim 3, the tapered edge of the cutter being oriented at an oblique angle relative to a longitudinal axis defined by the cutter.

5. The core needle biopsy device of claim 1, the piercer being configured to transport issue samples through a lumen defined by the piercer to a tissue sample holder associated with the core needle biopsy device.

6. The core needle biopsy device of claim 1, the drive assembly including a cutter drive and a piercer drive, the cutter drive being configured to cock and fire the cutter, the piercer drive being configured to cock and fire the piercer.

7. The core needle biopsy device of claim 6, the cutter drive and the piercer drive being operable independently of each other to cock and fire the cutter and the piercer, respectively.

8. The core needle biopsy device of claim 6, the cutter drive and the piercer drive each including a manipulator, a driver, and a spring, respectively, each manipulator being movable relative to a fixed portion of the respective spring to move the driver to a cocked position.

9. The core needle biopsy device of claim 8, each manipulator including a rack, the rack being configured to be driven by a motor to translate each manipulator proximally and distally.

10. The core needle biopsy device of claim 6, the cutter drive being oriented distally of the piercer drive.

11. The core needle biopsy device of claim 6, the cutter, the piercer, the cutter drive, and the piercer drive being all oriented co-axially with each other.

12. The core needle biopsy device of claim 6, at least a portion of the cutter driver defining an open proximal end such that the open proximal end is configured to permit the piercer to extend proximally past the cutter driver.

13. The core needle biopsy device of claim 1, the distal tip of the cutter being oriented at an angle defined by a longitudinal axis of the cutter.

14. A needle assembly for use in a biopsy device, the needle assembly comprising:
   (a) a hollow piercer having a sharp tip configured to penetrate tissue and a lateral aperture; and
   (b) a cutter disposed coaxially around the piercer and having a distal cutting edge, a swaged portion proximate to the distal cutting edge, and a cannula portion extending proximally from the swaged portion,
   a portion of the swaged portion forming a seal between the cutter and the piercer, the cannula portion defining a lumen disposed between the interior of the cutter and the exterior of the piercer,
   the lumen being configured to provide communication of atmospheric air to the lateral aperture of the piercer to permit the transport of a tissue sample through the piercer.

15. The needle assembly of claim 14, the swaged portion of the cutter being defined by a taper in a diameter of the cutter, the swaged portion being tapered inwardly as the cutter extends distally towards the distal cutting edge.

16. The needle assembly of claim 14, the piercer defining a lumen extending from the lateral aperture to a proximal end of the piercer.

17. The needle assembly of claim 16, the lumen of the piercer being configured to communicate tissue samples from the lateral aperture to a tissue sample holder in communication with the proximal end of the piercer.

18. A core needle biopsy device, comprising:
   (a) a body;
   (b) a drive assembly disposed within at least a portion of the body;
   (c) a needle assembly extending distally from the body and in communication with the drive assembly, the needle assembly including:
      (i) a piercer, the piercer defining a sharp tip, a lateral aperture, and a lumen in communication with the lateral aperture, and
      (ii) a hollow cutter, the cutter defining an elongate cannula, distal tip, and a swaged portion disposed between the cannula and the distal tip, the swaged portion being tapered relative to the cannula form a gap between the piercer and the cutter extending proximally from the distal tip; and
   (d) a tissue sample holder in communication with the lumen of the piercer, the gap being configured to selectively supply atmospheric air to the lateral aperture of the piercer to permit the transport of one or more tissue samples though the lumen of the piercer and into the tissue sample holder.

19. The core needle biopsy device of claim 18, the cutter being in communication with a continuous supply of atmospheric air.

20. The core needle biopsy device of claim 18, the cutter being in communication with a source of positive pressure, the being configured to communicate positive pressure to the lateral aperture of the piercer to force the one or more tissue samples through the lumen of the piercer.

* * * * *